US008298489B1

(12) United States Patent
Chen

(10) Patent No.: US 8,298,489 B1
(45) Date of Patent: Oct. 30, 2012

(54) ELECTRONIC INCENSE ASSEMBLY

(75) Inventor: Po-Chou Chen, New Taipei (TW)

(73) Assignee: Hon Hai Precision Industry Co., Ltd., Tu-Cheng, New Taipei (TW)

( * ) Notice: Subject to any disclaimer, the term of this patent is extended or adjusted under 35 U.S.C. 154(b) by 0 days.

(21) Appl. No.: 13/456,243

(22) Filed: Apr. 26, 2012

(30) Foreign Application Priority Data

Dec. 15, 2011 (TW) .................................. 100146404

(51) Int. Cl.
*A61L 9/00* (2006.01)

(52) U.S. Cl. ........................................ 422/126; 422/120
(58) Field of Classification Search .................. 422/120, 422/126
See application file for complete search history.

(56) References Cited

U.S. PATENT DOCUMENTS

| 7,934,845 | B2 * | 5/2011 | Yang | 362/101 |
| 2006/0227574 | A1 * | 10/2006 | Chien | 362/641 |
| 2009/0123345 | A1 * | 5/2009 | Yang | 422/124 |

* cited by examiner

*Primary Examiner* — Sean E Conley
(74) *Attorney, Agent, or Firm* — Altis Law Group, Inc.

(57) ABSTRACT

An electronic incense assembly includes a first tube, a second tube, a light source, two electrodes, and two wires. The first tube includes a first opaque coating on the outer surface thereof, a first end, and a second end. The first tube defines a first through hole. The second tube includes a second opaque coating on the outer surface thereof and defines a second through hole. The second end of the first tube is sleeved on the second tube. The first through hole communicates with the second through hole. The light source is positioned on the first end and covers the first through hole. The two electrodes are received in the second tube but extend across and out of the second tube. The two wires connect the light source to the two first electrodes.

2 Claims, 2 Drawing Sheets

ELECTRONIC INCENSE ASSEMBLY

BACKGROUND

1. Technical Field

The present disclosure relates to electronic incense sticks and, particularly, to an electronic incense assembly which can be powered to light when separated from an electronic burner.

2. Description of Related Art

Electronic incense sticks are typically integrated with electronic burners. In particular, light sources are received in the burner. The electronic incense sticks are stuck in the burner. Each electronic incense stick is a tube having an opaque coating on the outer surface and a transparent bubble on the upper end and guide light emitted form the light source to the transparent bubble to simulate a burning incense stick. However, the electronic incense sticks cannot be separated from the electronic burner or, at least, do not appear burning-like when separated from the electronic burners.

Therefore, it is desirable to provide an electronic incense assembly, which can overcome the above-mentioned shortcomings.

DETAILED DESCRIPTION

Embodiments of the disclosure will be described in detail, with reference to the accompanying drawings.

Figure 1:
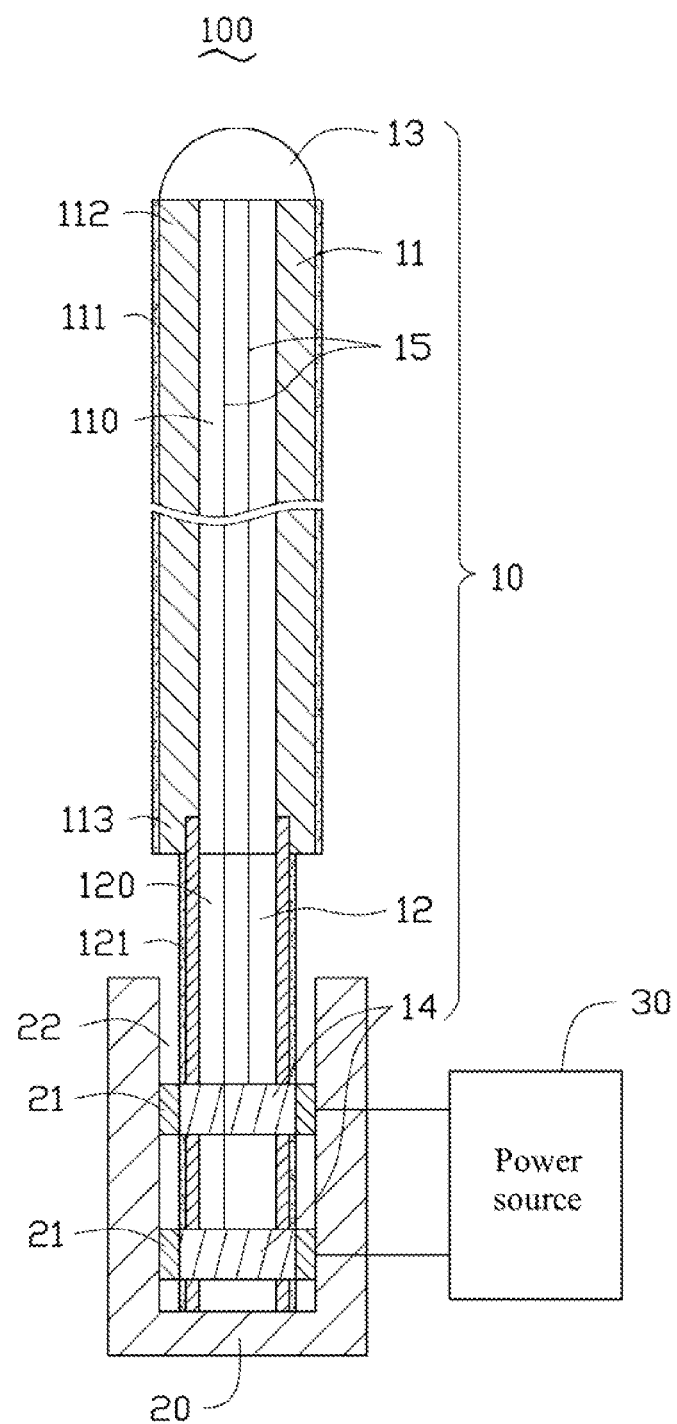
FIG. 1 is a cross-sectional schematic view of an electronic incense assembly, according to an embodiment, the electronic incense assembly including an electronic incense stick.
Figure 2:
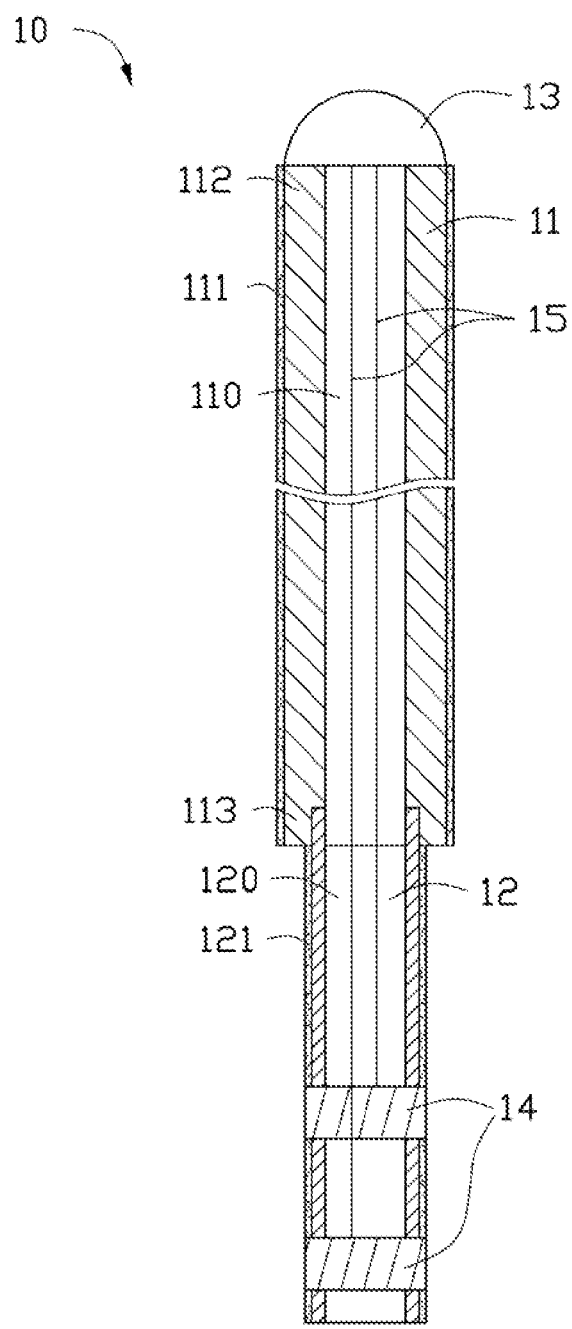
FIG. 2 is a cross-sectional schematic view of the electronic incense stick.

Referring to FIGS. 1-2, an electronic incense assembly 100, according to an embodiment, includes an electronic incense stick 10, a socket 20, and a power source 30.

The electronic incense stick 10 includes a first tube 11, a second tube 12, a light source 13, two first electrodes 14, and two wires 15.

The first tube 11 defines a circular first through hole 110 generally at the center thereof. The second tube 12 defines a circular second through hole 120 generally at the center thereof. The first tube 11 is sleeved on the second tube 12 and the first central through hole 110 communicates with the second central through hole 120. In one embodiment, the diameters of the first through hole 110 and the second through hole 120 are substantially equal to each other.

The second tube 12 is for simulating the bone of incense sticks that is left without incense coating for hand holding. The first tube 11 is for simulating the incense coating of the incense sticks. Therefore, the first tube 11 has a first opaque coating 111 on the outer surface thereof, which has the same color of the incense coating of the incense sticks, such as yellow, red, or black. The second tube 12 has a second opaque coating 121 on the outer surface thereof, which has the same color of the bone of the incense sticks, such as yellow or red.

The first tube 11 includes a first end 112 and a second end 113. The second end 113 is sleeved on an end of the second tube 12.

The light source 13 is bubble-shaped and can be a bulb or a light emitting diode assembly. The light source 13 is positioned on the first end 112 and covers the first through hole 110.

The two first electrodes 14 are plates in shape and are held in and across the second tube 12, and are exposed out from the second tube 12.

The two wires 15 are connected to the light source 13, run in the first through hole 110 and the second through hole 120, and are connected to the two first electrodes 14, respectively.

The electronic incense stick 10 can be stuck into a socket 20 and thus is connected to the power source 30.

The socket 20 defines a groove 22 for fittingly receiving the second tube 12 and includes two second electrodes 21. The two second electrodes 21 are hollow plates in shape and attached to the sidewall of the groove 22 and are configured for receiving and contacting the first electrodes 14 respectively when the second tube 12 is received in the groove 22.

The power source 30 such as a battery can be attached to the socket 20 and connected to the second electrodes 21.

In assembly, the second tube 12 is received in the groove 22 and the first electrodes 14 contact the second electrodes 21 respectively. The light source 13 is electrically connected to the power source 30 via the two wires 15, the first electrodes 14, and the second electrodes 21 and is lit as powered by the power source 30. As such, the electronic incense assembly 100 can be separated from the burner and can be powered to light without contact with the burner.

Particular embodiments are shown here and described by way of illustration only. The principles and the features of the present disclosure may be employed in various and numerous embodiments thereof without departing from the scope of the disclosure as claimed. The above-described embodiments illustrate the scope of the disclosure but do not restrict the scope of the disclosure.

What is claimed is:

1. An electronic incense assembly, comprising:
    a first tube comprising a first outer surface, a first opaque coating on the first outer surface, a first end, and a second end, the first tube defining a first through hole;
    a second tube comprising a second outer surface, a second opaque coating on the second outer surface and defining a second through hole, the second end of the first tube being sleeved on the second tube, the first through hole communicating with the second through hole;
    a light source positioned on the first end and covering the first through hole;
    two first electrodes received in the second tube but extending across and out of the second tube; and
    two wires connecting the light source to the two first electrodes.

2. The electronic incense assembly of claim 1, further comprising:
    a socket defining a groove receiving the second tube and including two second electrodes, the two second electrodes being hollow plates in shape, and attached to a sidewall of the groove, and receiving and contacting the first electrodes respectively; and
    a power source electrically connected to the second electrodes.

* * * * *